United States Patent
Huang et al.

(10) Patent No.: US 6,981,323 B2
(45) Date of Patent: Jan. 3, 2006

(54) METHOD FOR FABRICATING A FLUID INJECTION HEAD STRUCTURE

(75) Inventors: Tsung-Wei Huang, Taipei (TW); Chih-Ching Chen, Taipei (TW)

(73) Assignee: BenQ Corporation, Tao-Yuan Hsien (TW)

( * ) Notice: Subject to any disclaimer, the term of this patent is extended or adjusted under 35 U.S.C. 154(b) by 1 day.

(21) Appl. No.: 10/708,152

(22) Filed: Feb. 11, 2004

(65) Prior Publication Data
US 2004/0160479 A1   Aug. 19, 2004

Related U.S. Application Data

(62) Division of application No. 10/065,609, filed on Nov. 3, 2002, now Pat. No. 6,902,257.

(30) Foreign Application Priority Data
Nov. 8, 2001   (TW) ............................... 90127720 A

(51) Int. Cl.
  *B21D 53/76* (2006.01)
  *B41J 2/135* (2006.01)
(52) U.S. Cl. ...................... 29/890.1; 29/25.35; 29/594; 29/830; 29/831; 347/45
(58) Field of Classification Search ............. 29/25.35, 29/890.1, 830, 831, 594; 347/45, 48, 58, 347/59, 63, 65; 216/94, 99, 100, 79, 27
See application file for complete search history.

(56) References Cited

U.S. PATENT DOCUMENTS

| | | | |
|---|---|---|---|
| 4,887,098 A | | 12/1989 | Hawkins et al. |
| 5,122,812 A | * | 6/1992 | Hess et al. ..................... 347/59 |
| 5,159,353 A | * | 10/1992 | Fasen et al. .................. 347/59 |
| 5,322,811 A | * | 6/1994 | Komuro et al. ............... 438/21 |
| 5,422,505 A | * | 6/1995 | Shirai ......................... 257/327 |
| 5,774,148 A | * | 6/1998 | Cornell et al. ................ 347/59 |
| 6,102,530 A | * | 8/2000 | Kim et al. .................... 347/65 |
| 6,184,428 B1 | | 2/2001 | Zahoor et al. |
| 6,471,338 B2 | * | 10/2002 | Chen et al. ................... 347/59 |

FOREIGN PATENT DOCUMENTS

| | | |
|---|---|---|
| DE | 39 06 484 A1 | 9/1990 |
| EP | 0 924 079 A2 | 6/1999 |
| JP | 55-132259 | 10/1980 |
| JP | 62-240558 | 10/1987 |

* cited by examiner

*Primary Examiner*—A. Dexter Tugbang
*Assistant Examiner*—Tai Van Nguyen
(74) *Attorney, Agent, or Firm*—Winston Hsu

(57) ABSTRACT

The present invention provides a fluid injection head structure and a method of fabricating the same. The fluid injection head structure is disposed on a substrate and has a bubble generator, a functional device for control the bubble generator, a first conductive trace composed of poly-silicon, a chamber, a manifold in flow communication with the chamber, and a second conductive trace. The second conductive trace electrically couples the functional device with the bubble generator and the first conductive trace. Moreover, the chamber further has at least one orifice through the substrate and a gate and the first conductive trace are formed in the same photo-etching process (PEP).

15 Claims, 12 Drawing Sheets

METHOD FOR FABRICATING A FLUID INJECTION HEAD STRUCTURE

CROSS REFERENCE TO RELATED APPLICATIONS

This application is a division of U.S. application Ser. No. 10/065,609 filed Nov. 03, 2002 now U.S. Pat. No. 6,902,257.

BACKGROUND OF INVENTION

1. Field of the Invention

The present invention relates to a fluid injection head structure, and more particularly, to a fluid injection head structure with conductive traces made of one single metal layer and one single poly-silicon layer.

2. Description of the Prior Art

Fluid injection devices are widely applied in ink jet printers. As a reliability of ink jets have improved, the cost of manufacturing ink jets has reduced significantly. Ink jets offering high-quality droplets with a high frequency and a high spatial resolution are commonplace. Fluid injection devices can be applied to many other fields in advance, such as fuel injection systems, cell sorting, drug delivery systems, print lithography, and micro jet propulsion systems.

Among all available products, some use a method of center feeding for ink supply, such as the model of C6578 cartridge of the Hewlett-Packard Company, and some use a method of edge feeding, such as the model of HP51645 cartridge of the Hewlett-Packard Company. In the former method, a sand blasting, laser drilling, or chemical etching process is performed to create a manifold through the center of the chips for feeding ink. However, this method requires a large chip size, and the area above the manifold is wasted, leading to needlessly high manufacturing costs. Although the process of penetrating through chips is not needed in the latter method, two metal layers and a poly-silicon layer are still needed. Therefore, many photo masks are used, and both the time and cost of fabrication are increased.

U.S. Pat. No. 5,774,148, "Print head with field oxide as thermal barrier in chip", mentions a method for transmitting signals. A second metal layer is electrically connected to a first metal layer through a via and signals are transmitted between a heater 44 and a MOSFET device. Additionally, a poly-silicon layer is used as a gate of MOSFET device and a contact layer is used to electrically connect to the first metal layer for transmitting signals.

SUMMARY OF INVENTION

It is therefore a primary objective of the present invention to provide a fluid injection head structure and a method of manufacturing the same with conductive traces made of one metal layer and one poly-silicon layer to simplify the manufacturing process and lower manufacturing costs.

In a preferred embodiment, the fluid injection head structure comprises a substrate, a bubble generator, a functional device to control the bubble generator, a first conductive trace made of a poly-silicon layer, a chamber, a manifold connected to the chamber such that fluid can flow through the manifold to the chamber, and a second conductive trace to electrically connect to the functional device and the bubble generator, and the functional device and the first conductive trace. In addition, the chamber further comprises an orifice in a top surface of the substrate. Moreover, a gate of the functional device and the first conductive trace are formed in the same photo-etching process (PEP).

It is an advantage of the present invention that only one metal layer and one poly-silicon layer are used as conductive layers of the fluid injection head structure. The present invention overcomes the problem of time delay and heat generation. The fabrication method of the present invention also helps to reduce manufacturing expenses and fabrication time.

These and other objectives of the present invention will no doubt become obvious to those of ordinary skill in the art after reading the following detailed description of the preferred embodiment, which is illustrated in the various figures and drawings.

DETAILED DESCRIPTION

Figure 1:
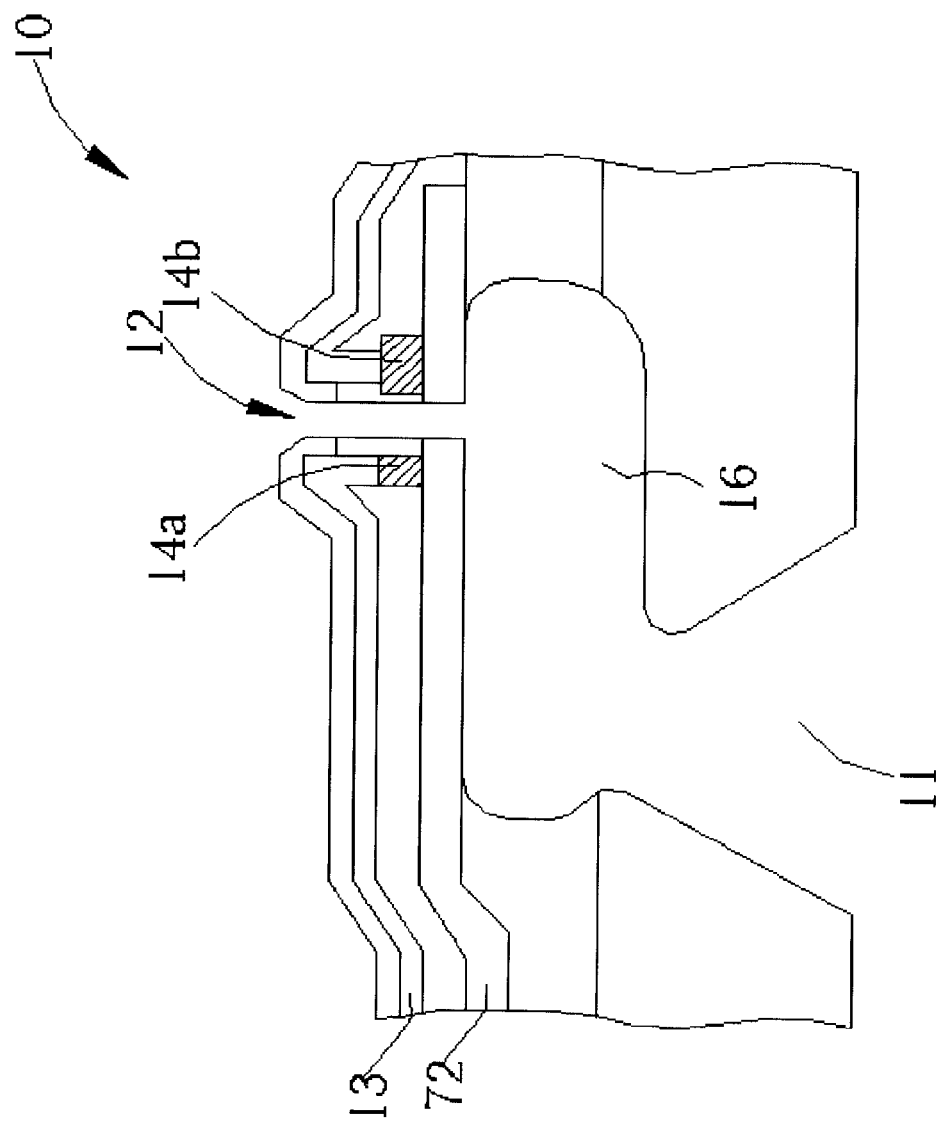
FIG. 1 is a cross-sectional diagram of a print head structure according to the present invention.

Please refer to FIG. 1, which is a cross-sectional diagram of a print head structure according to the present invention. A fluid injection head structure with a virtual valve is used in the present invention. As shown in FIG. 1, a bubble generator 14 comprises two bubble generating devices, a first heater 14a and a second heater 14b, disposed adjacent to an orifice 12. Because of differences, such as different resistances, between the two heaters 14a, 14b, when the two heaters 14a, 14b heat fluid (not shown) inside the chamber 16, two bubbles are generated in turn. A first bubble (not shown) is generated by the first heater 14a, closer to a manifold 11 than the second heater 14b, wherein the first bubble isolates the manifold 11 from an orifice 12 and acts as a virtual valve to reduce a cross talk effect between this chamber 16 and neighboring chambers 16. Then, a second bubble (not shown) is generated by the second heater 14b. The second bubble squeezes fluid, such as ink, inside the chamber 16 to eject out of the orifice 12. Finally, the second bubble combines with the first bubble so as to reduce the generation of satellite droplets.

The fluid injection head structure of the present invention feeds ink successfully without fully etching through the chips. Based on this structure, power line layouts can be designed above the manifold 11. Not counting the resistance layers, only one single poly-silicon layer and one single metal layer (SPSM) process is performed in the present invention.

Figure 2:
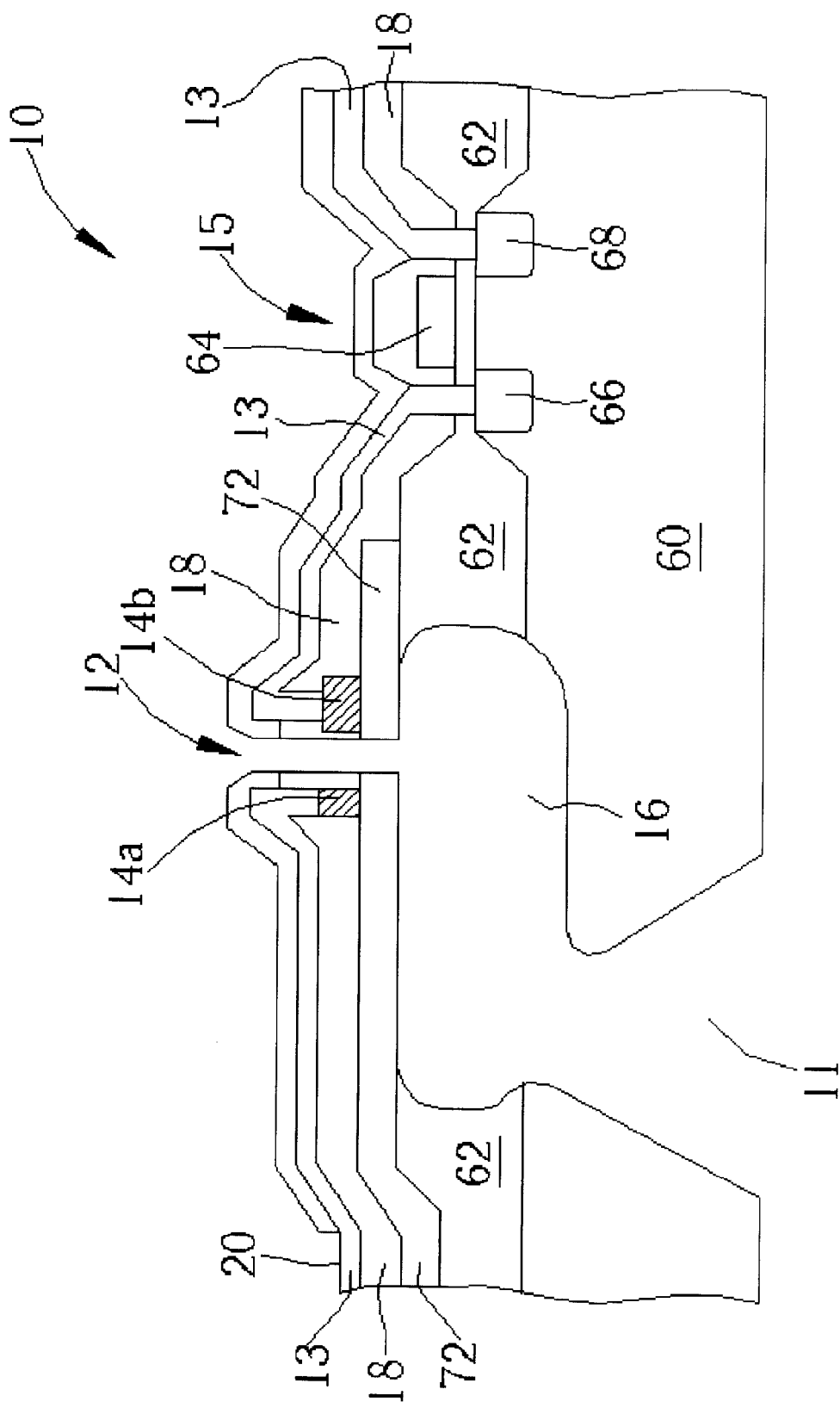
FIG. 2 is a cross-sectional diagram of a fluid injection head structure of an embodiment according to the present invention.

Please refer to FIG. 2, which shows a cross-sectional diagram of a fluid injection head structure according to the present invention. A low temperature oxide layer 18 is deposited on top of the bubble generator 14. After that, a via layer is formed in a predetermined area and a metal layer 13 is deposited on the top surface of the heaters 14a and 14b through the via layer. Thus, the metal layer 13 is electrically connected to the heaters 14a and 14b.

In the same manner, a drain 68 and a source 66 of a MOSFET 15 are electrically connected to the heaters 14a and 14b, and a ground 20 via the metal layer 13. When a gate 64 of the MOSFET 15 is turned on, an external voltage signal is applied to the print head from a pad of the metal layer 13. A current flows from the pad via the metal layer 13 to the first heater 14a and the second heater 14b. Then, the current passes through the drain 68 and the source 66 to the ground 20 so as to complete a heating process. As the ink inside the chamber 16 is heated, two bubbles are generated to squeeze ink droplets out of the orifice 12. It dependents upon the data to be printed to control which orifice 12 ejects ink droplets during a printing process. The material of the metal layer 13 is any one of aluminum, gold, copper, tungsten, alloys of aluminum-silicon-copper, or alloys of aluminum-copper.

Figure 3:
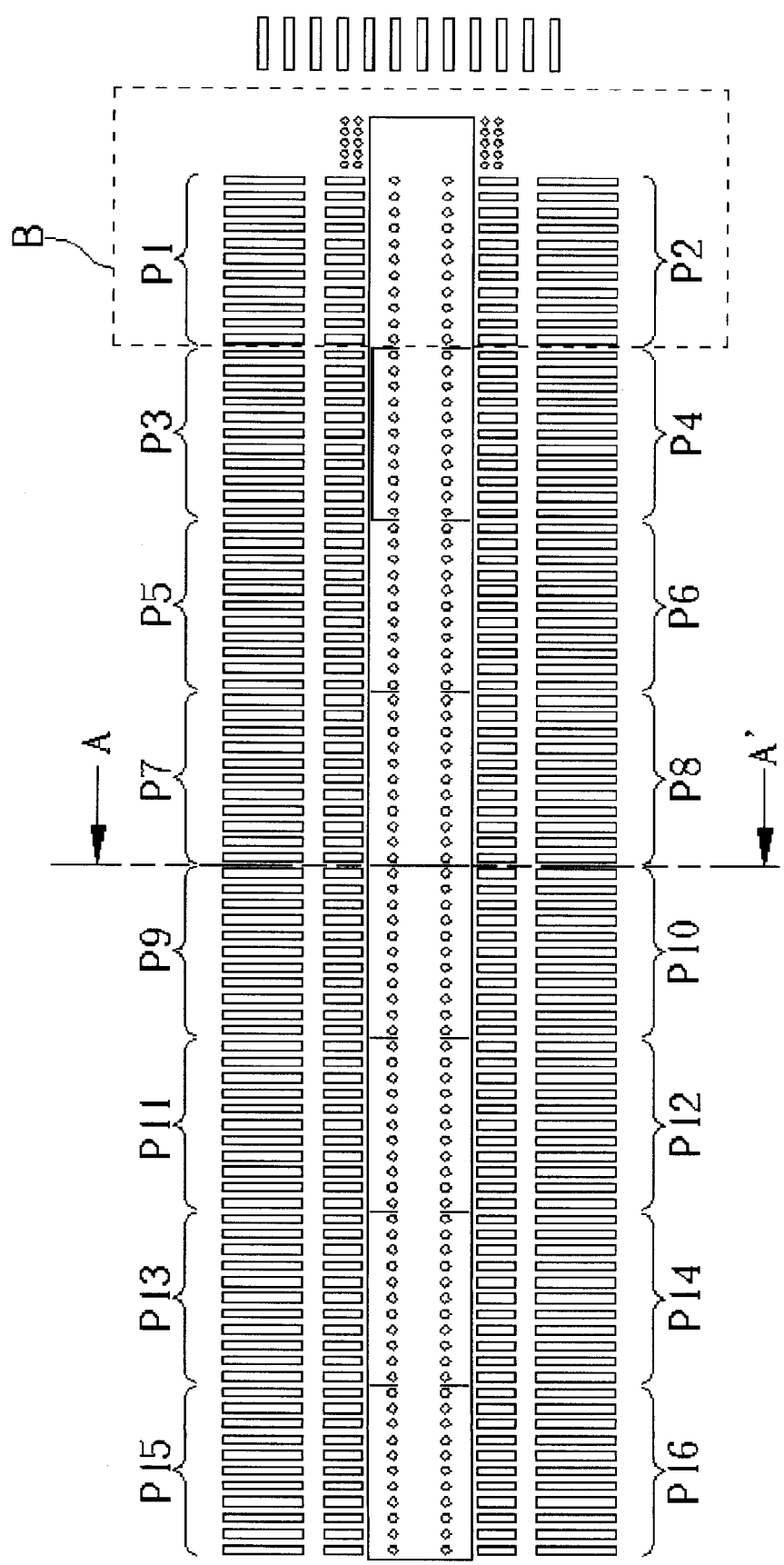
FIG. 3 is a top view of the fluid injection head structure of the present invention.
Figure 4:
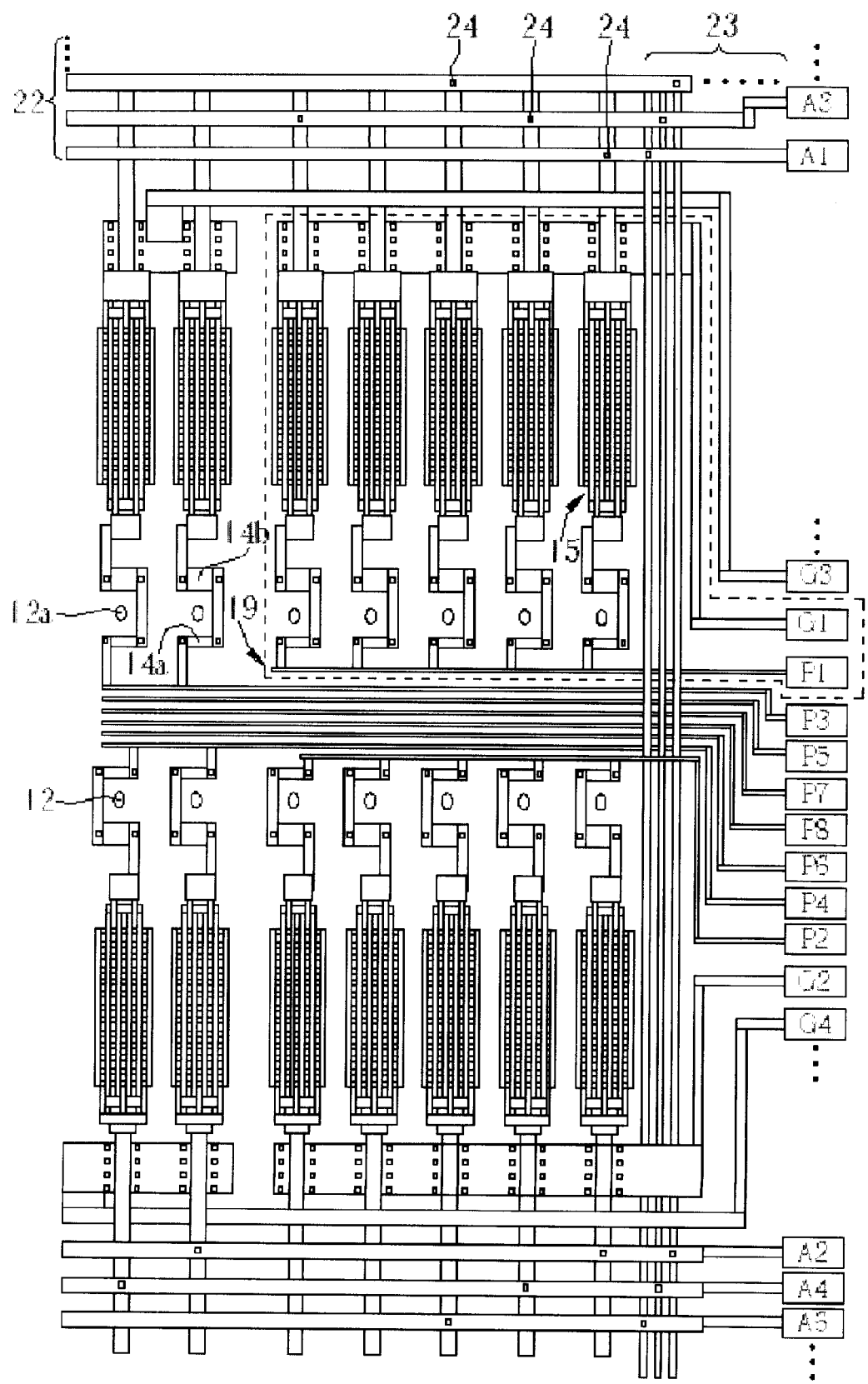
FIG. 4 is a local amplified diagram of the fluid injection head chip shown in FIG. 3.
Figure 5:
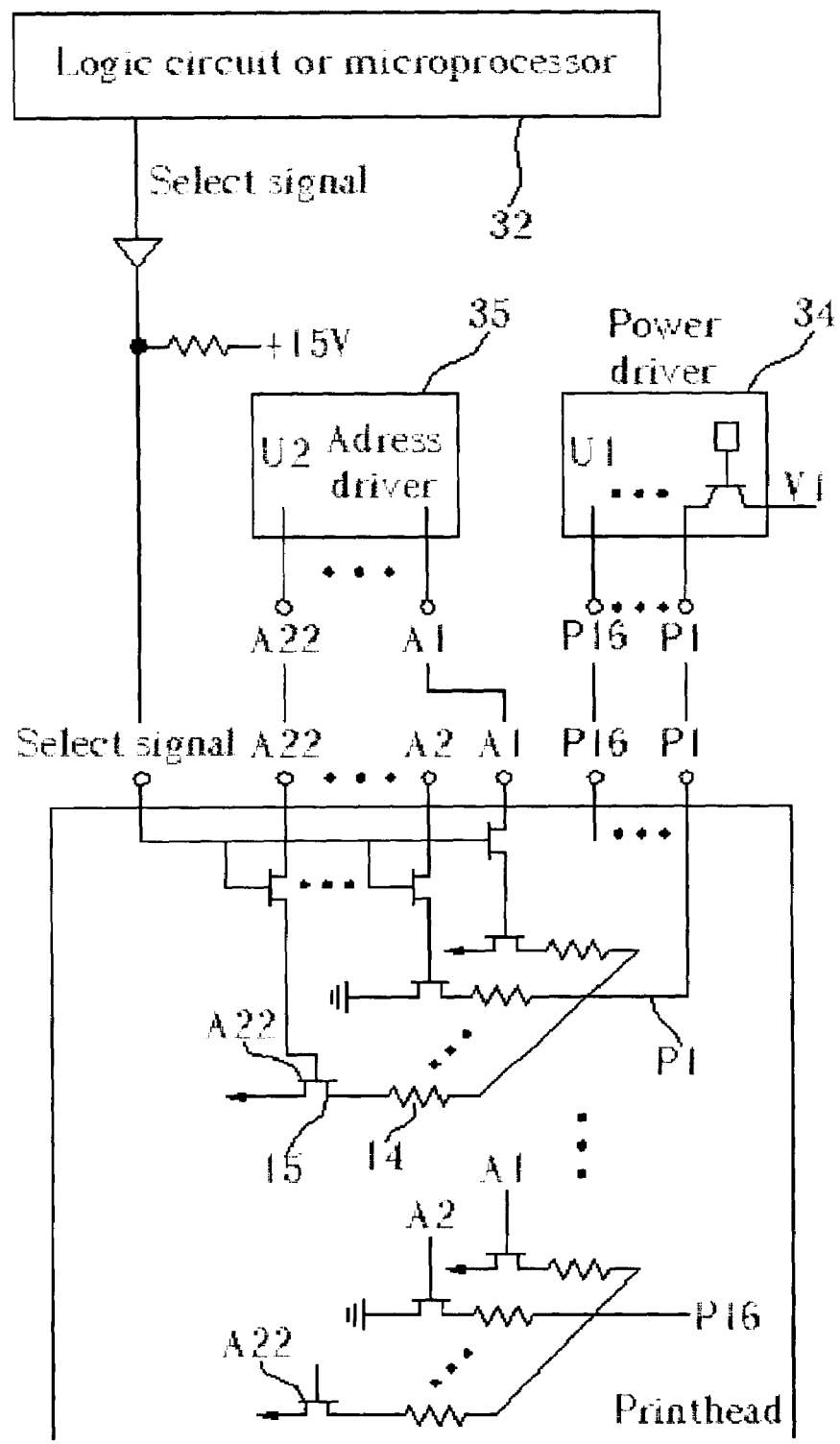
FIG. 5 is a schematic diagram of a matrix driving circuit in the fluid injection head of the present invention.

Please refer to FIG. 3 and FIG. 4. FIG. 3 is a top view of the print head according to the present invention. In the preferred embodiment, the orifice 12 of the print head is divided into sixteen P groups, P1 to P16, and each P group comprises twenty-two addresses A1 to A22. As shown in FIG. 5, which shows a schematic diagram of a matrix driving circuit, a select signal is generated by a logic circuit or a microprocessor 32 according to the data to be printed. Then, the select signal is transmitted to a power driver 34 and an address driver 35 to determine which A (A1 to A22) should be turned on and to which P (P1 to P16) the power should be provided. For example, providing power to P1 and turning on A22, the heaters 14a and 14b on the MOSFET 15 of P1A22 will complete an operation of heating and ejecting ink at the predetermined time.

FIG. 4 is a local amplified diagram of the region B shown in FIG. 3. Two rows of orifices 12 are positioned on the center of the chip. Dividing the orifices into two parts by a line A–A" shown in FIG. 3, there are eight groups comprising P1 to P8 on the right and eight groups comprising P9 to P16 on the left. The place above the manifold 11 between the two rows of orifices 12 is used for a power line layout. Eight metal power lines corresponding to P1 to P8 are positioned to the right of the line A–A" and electrically connected to I/O pads on the right. In the same manner, eight power lines corresponding to P9 to P16 (not shown) are positioned on the left of the line A–A" and electrically connected to I/O pads on the left.

The driving circuit between each corresponding P pad and G pad uses a U-type circuit layout. The driving circuit between the pad P1 and the pad G1 is illustrated in a dashed block in FIG. 4. Each driving circuit is connected without crossing any other driving circuit. Only one metal layer 13 is used to form the power line 19 between the heaters 14a, 14b and the grounding pad G. There are eleven metal lines 22 positioned above the groups of MOSFET 15 and another eleven metal lines 22 positioned below the groups of MOSFET 15 in the page 4. The metal lines 22 are electrically connected to the pads A so as to transmit the output data of the address driver 35 to the corresponding MOSFET 15 to control ink ejection. There are also eleven poly-silicon lines 23 positioned to the left of the groups of MOSFET 15 and another eleven to the right of the groups of MOSFET 15.

Then, contact layers 24 are formed to electrically connect the metal lines 22 and the poly-silicon lines 23 to complete the connection of the driving circuits. The poly-silicon lines 23 are used to connect the metal lines 22 above and below the groups of MOSFET 15 (i.e. the upper parts and lower parts of the metal lines 22 in the FIG. 4). For example, if a signal is input from the pad A1 to turn on the heaters of P16, it has to be transmitted via the poly-silicon lines 23 through the metal lines 22 to the heaters of P16.

Figure 5A:
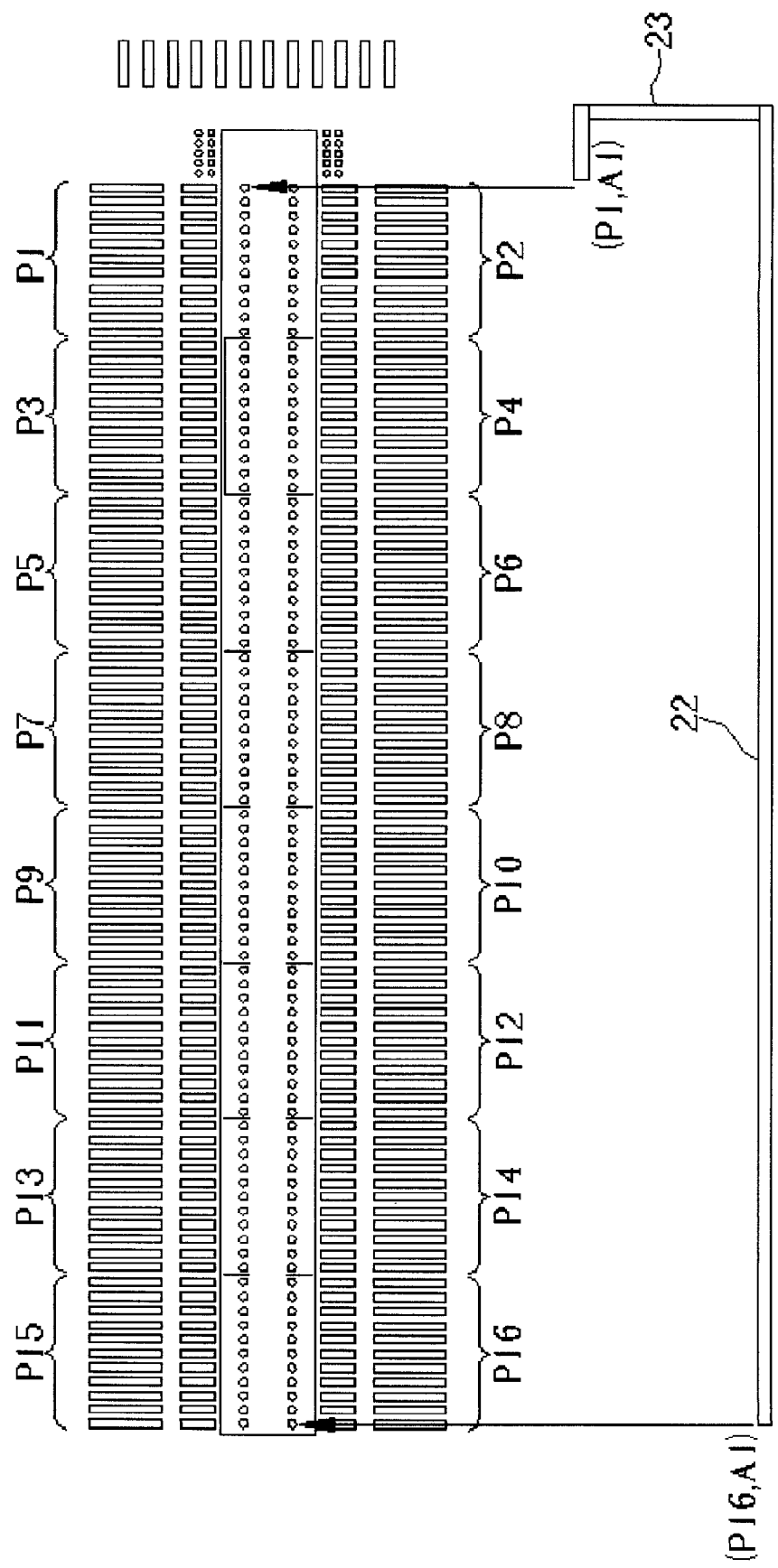
FIG. 5A is a schematic diagram of transmitting signals through address lines.
Figure 5B:
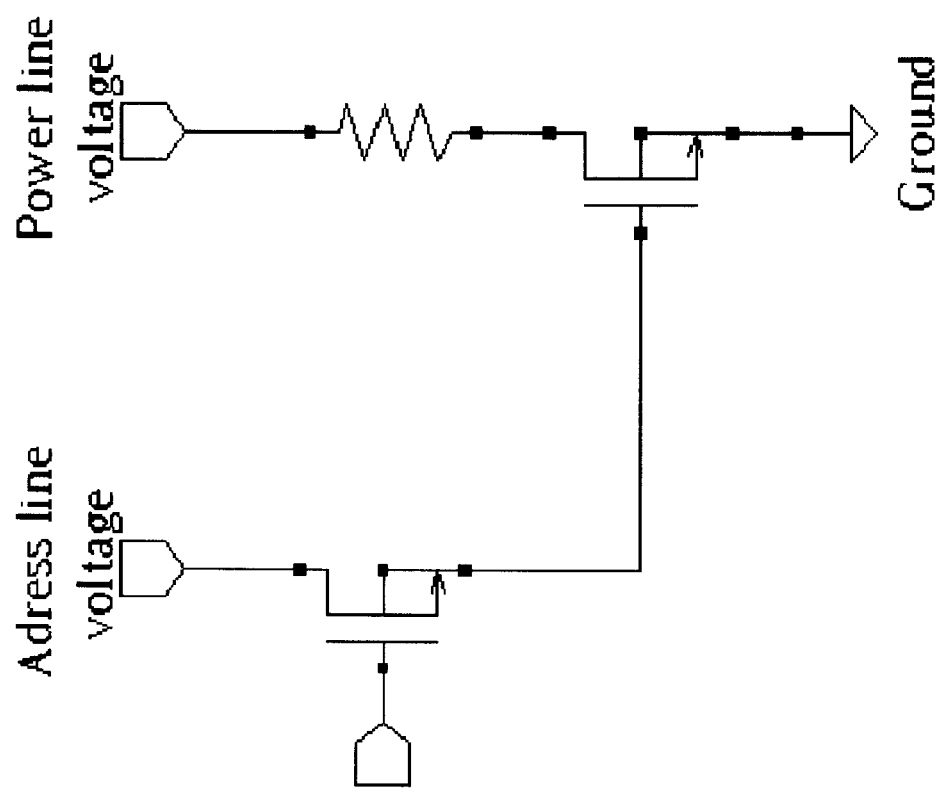
FIG. 5B is an equivalent circuit of the fluid injection head at P1-A1.
Figure 5C:
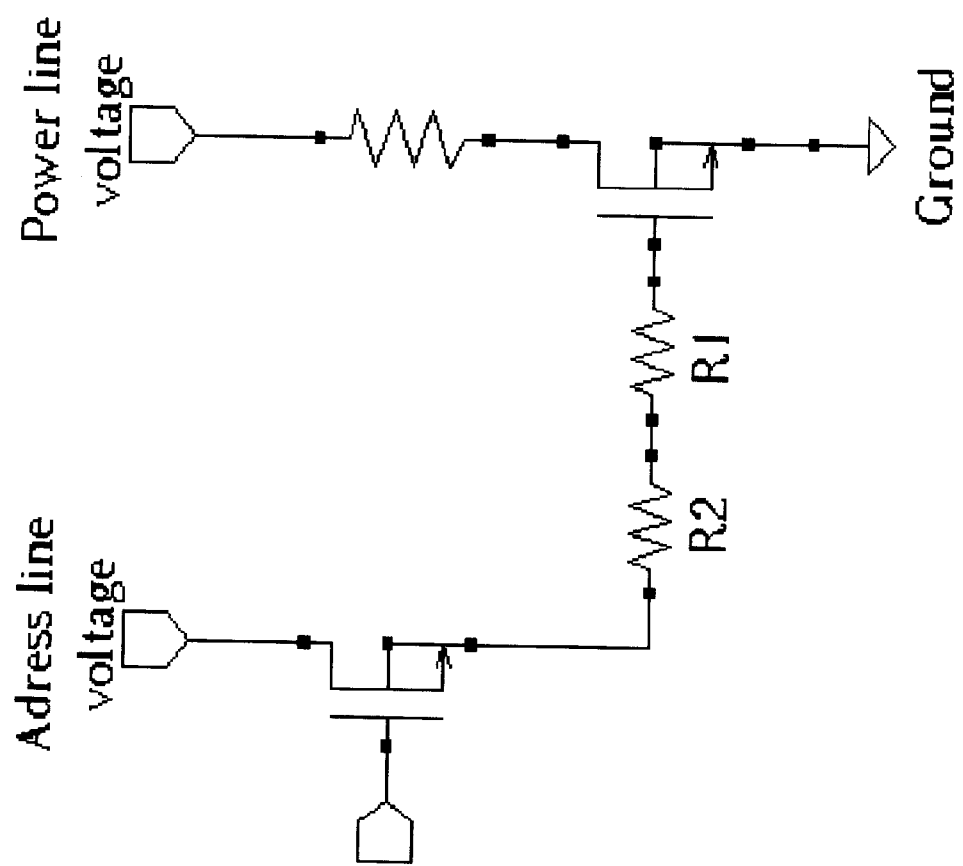
FIG. 5C is an equivalent circuit of the fluid injection head at P16-A1.

Please refer to FIG. 5A to FIG. 5D, which show schematic diagrams of circuits for transmitting signals with the silicon line 23 according to the present invention. Although a poly-silicon line 23 with a length of 2901 μm is used as an address conductive trace A1 to A22, the electrical characteristics of the circuits are not deteriorated. First, very little current exists in the gate 64 of the MOSFET 15 so the heat effect of the poly-silicon lines 23 can be ignored. Second, as shown in FIG. 5A, resistance in the conductive trace is increased due to the poly-silicon line 23 may occur the problem of time delay when the heaters in A1 of all P groups (including P1 to P16) inject. Take two A1 addresses with the largest distance between them, A1-P1 and A1-P16, as example. During printing operation, the frequency of ink-jet printing is set at about 10 KHz. Each address has a switching time of about 3.5 μs. Timing of a power supply for a P group must be within a pulse width of 3.5 μs so that the timing for power supply of a P group is about 2 μs. This means that there is only a time buffer of about 500 ns between each neighboring address. These limitations must be met or errors may occur. For example, in the group P1, the print head A1 stops and the print head A2 starts to inject, but the print head A1 in the group P16 may still be injecting.

Figure 5D:
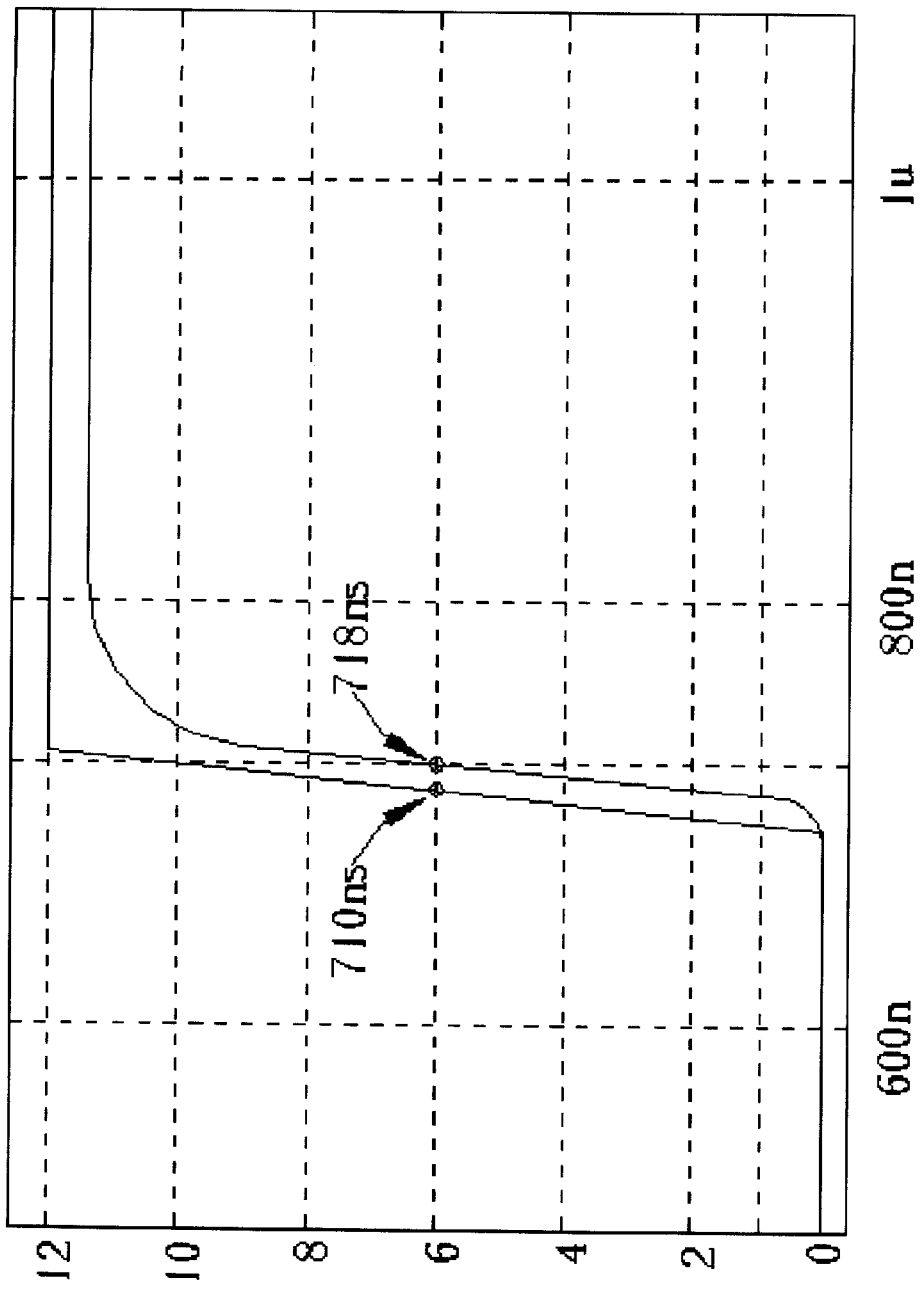
FIG. 5D is a schematic diagram of HSPICE simulate of the equivalent circuits shown in FIG. 5B and FIG. 5C.

Please refer to FIG. 5A. According to the sheet resistances of the metal line 22 (0.1 Ω/μm) and the poly-silicon line 23 (10 Ω/μm), the equivalent resistances of A1P1 and A1P16 while the gate 64 of all MOSFET device 15 is turned on can be obtained. The equivalent circuit of A1P1 circuit is shown as FIG. 5B and that of A1P16 circuit is shown as FIG. 5C. In contrast to A1P1, a signal must pass through additional poly-silicon line 23 and a metal line 22 when transmitted to A1P16. The resistance R1 of the additional poly-silicon line 23 is about 2901 Ω, and the resistance R2 of the additional metal line 22 is about 147 Ω. A HSPICE simulate is performed for these two circuits and a result is shown in FIG. 5D. Comparing time of the clock 50% of A1P1 and A1P16, which are 710 and 716 ns respectively, therefore, the time delay is only about 8 ns. Comparing to the time delay endurance of 500 ns, the time delay of the present invention has no influence on ink injecting.

Figure 6:
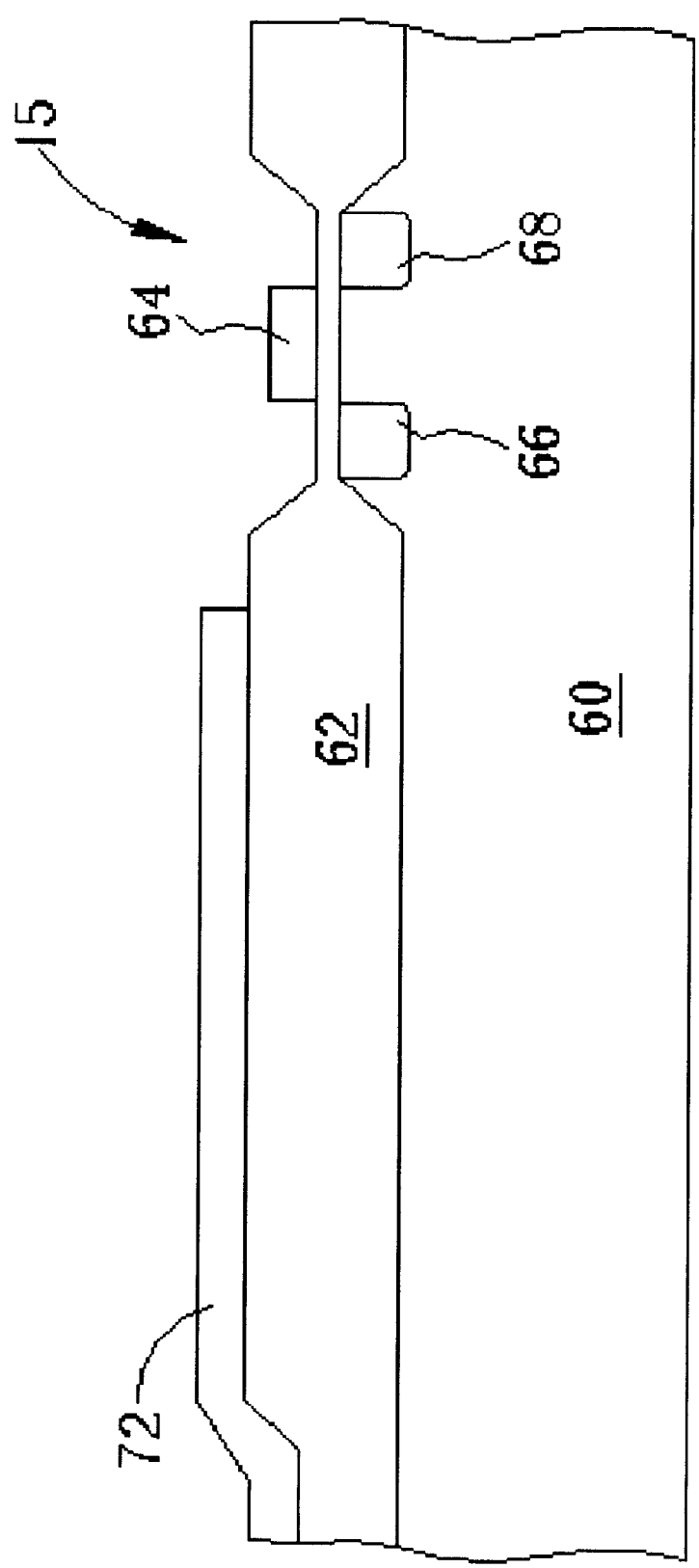
FIG. 6 to FIG. 8 are schematic diagrams of forming the fluid injection head according to the present invention.
Figure 7:
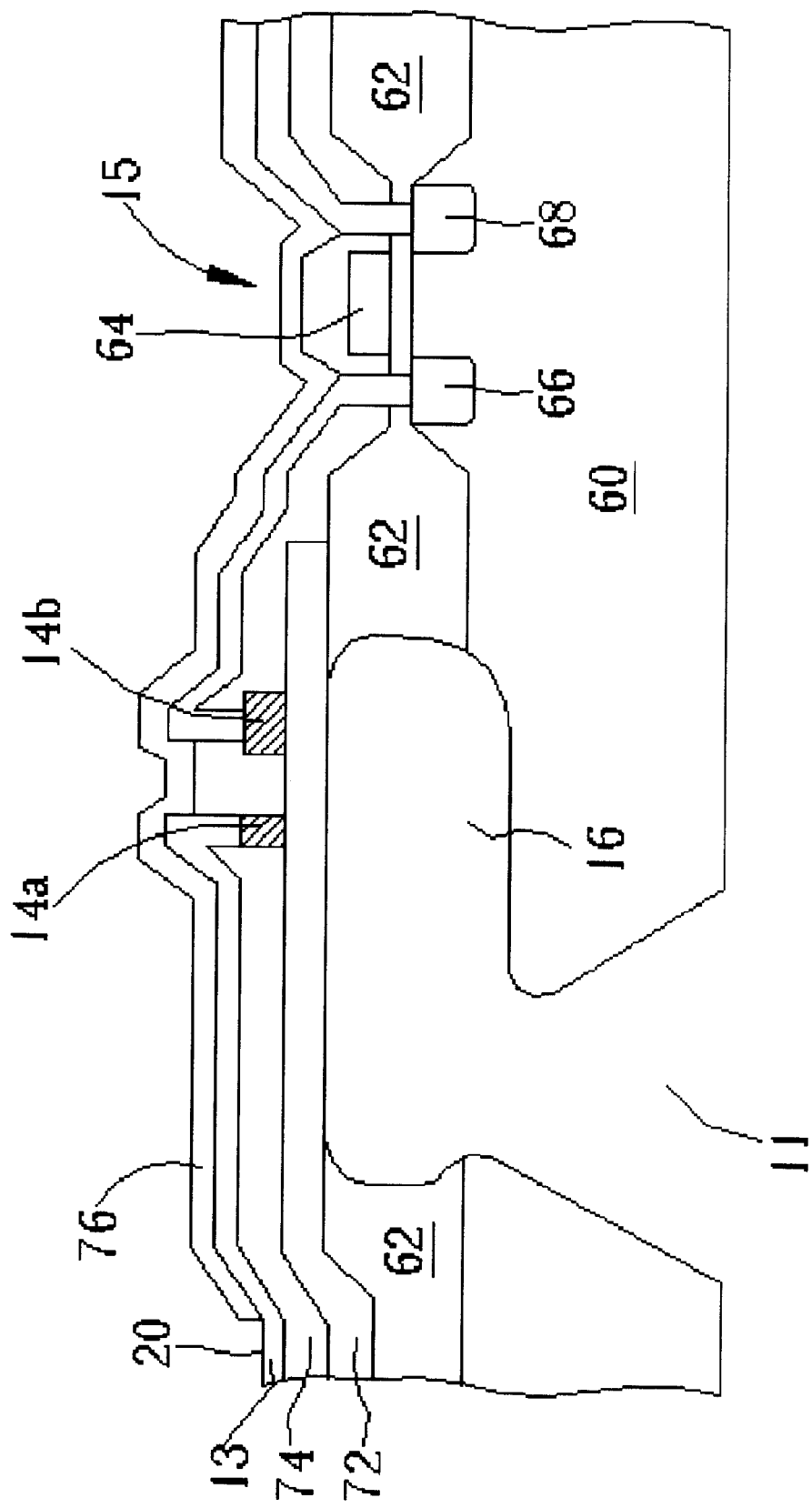
Figure 8:
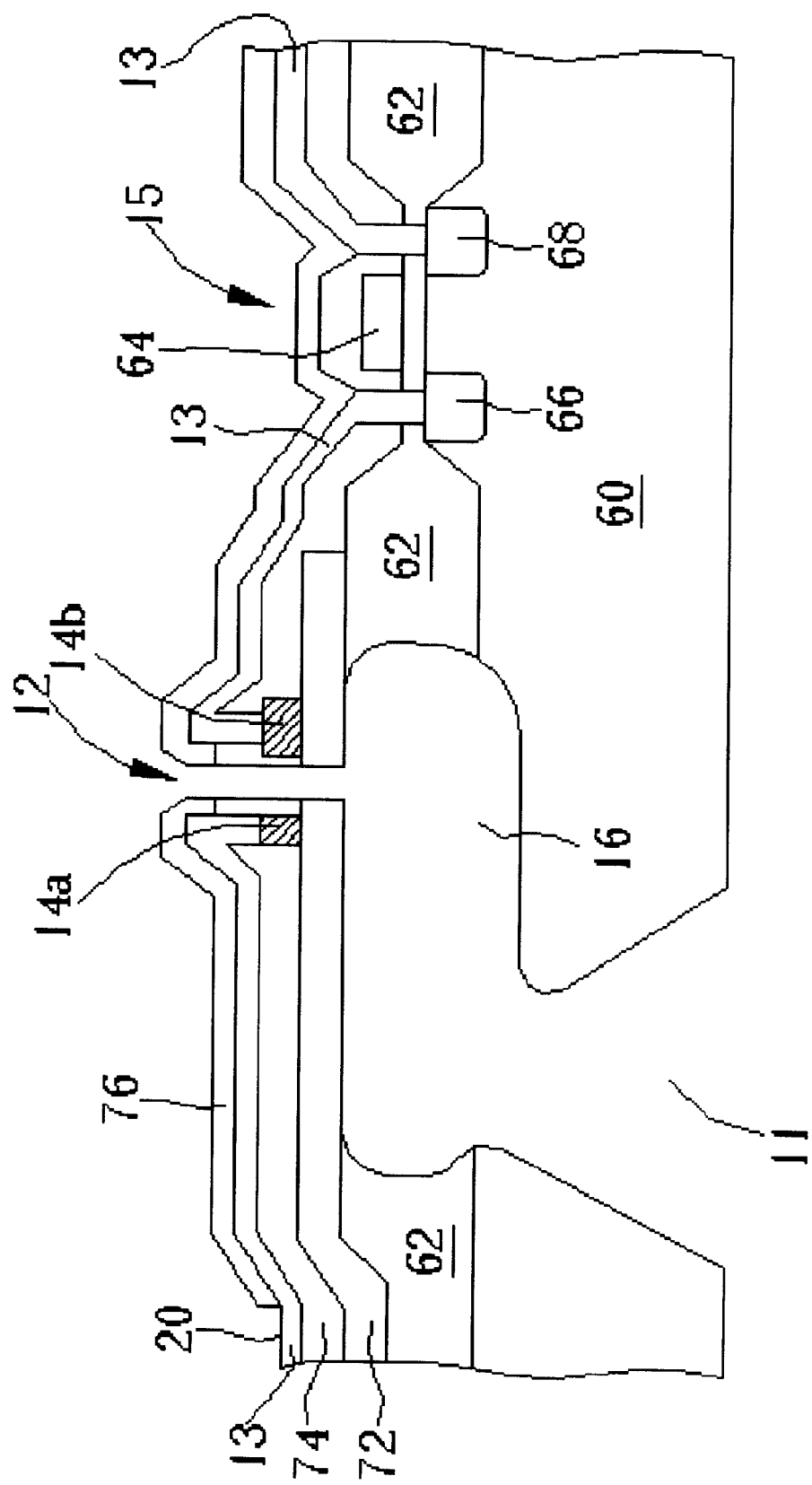

Please refer to FIG. 6 to FIG. 8, which show schematic diagrams of forming the fluid injection head according to the present invention. First, a local oxidation process is performed to form a field oxide layer 62 on a silicon substrate 60. A blanket boron implantation process is performed to adjust the threshold voltage of the driving circuit. A poly-silicon gate 64 is formed in the field oxide layer 62. At the same time, twenty-two poly-silicon lines 23 are formed on both edges of the chip. An arsenic implantation is performed to form a source 66 and a drain 68 on both sides of the gate 64. Then a low stress layer 72 such as silicon nitride is deposited to form an upper layer of the chamber 16 as shown in FIG. 6.

Please refer to FIG. 7. An etching solution (KOH) is used to etch a back side of substrate 60 to form a manifold 11 for fluid supply. Then the field oxide layer 62 is partially removed with an etching solution (HF) to form the chamber 16. After that, a precisely-timed etching process using KOH is performed to increase the depth of the chamber 16. The chamber 16 and the manifold 11 are connected and filled with fluid, however this etching process needs special attention because convex corners in the chamber 16 are also etched.

Next, a process of forming heaters is performed. This process should be obvious to those of ordinary skill in the art. A good choice of materials to use for the first heater 14a and the second heater 14b is alloys of tantalum and aluminum, but other materials like platinum or HfB$_2$ can also work effectively. A low temperature oxide layer 74 is deposited over the entire substrate 60. In addition to protecting the first heater 14a and the second heater 14b and isolating the MOSFET 15, the low temperature oxide layer 74 serves as a protective layer that covers the gate 64, the source 66, the drain 68, and the field oxide 62.

Next, a conductive layer 13 is formed on the first heater 14a and the second heater 14b to electrically connect the first heater 14a, the second heater 14b, and the MOSFET 15 of the driving circuit. The driving circuit transmits a signal to individual heaters and drives a plurality of pairs of heaters, so that fewer circuit devices and linking circuits are required. The preferred material for the conductive layer 13 is an alloy of aluminum-silicon-copper, aluminum, copper, gold, or tungsten. A low temperature oxide layer 76 is deposited as a protection layer on the conductive layer 13.

Please refer to FIG. 8. An orifice 12 is formed between the first heater 14a and the second heater 14b. So far, the specification has detailed the formation of a fluid injector array with a driving circuit integrated in one piece. The driving circuit and heaters are integrated on the same substrate and an integrated injection head structure is formed without the need for an attached nozzle plate.

The present invention uses a single poly-silicon and a single metal (SPSM) process to complete the circuit connection. The poly-silicon lines 23 and the gate 64 can be formed in a photo-etching process (PEP) to simplify the manufacturing process. The present invention not only avoids using a second metal layer, but also completes the function of the MOSFET 15 without affecting performance.

The following is a detailed description of the operation of the present invention. Please refer to FIG. 4 and FIG. 5. When printing starts, the logic circuit or microprocessor 32 determines which orifices 12 should eject ink according to the data to be printed and generates a select signal. The select signal is transmitted to the power driver 34 and the address driver 32 to turn on the proper A groups (A1 to A22) and apply power to the proper P groups (P1 to P16). Thus, a current is generated and applied to the heaters 14a and 14b to heat fluid and generate bubbles so that ink droplets are ejected. For example, suppose that a droplet is to be ejected from the orifice 12a of A1P1. First, a voltage signal is input from an I/O pad of A1 and transmitted to the gate 64 of MOSFET 15 to turn on the gate 64. Next, another voltage signal is input from an I/O pad of P1 to generate a current. The current passes via the heaters 14a and 14b to the drain 68, the source 66, and the ground 20 so as to heat the fluid and generate bubbles. The bubbles act to eject an ink droplet from the orifice 12a of A1P1.

Although the above description details a monochromatic printer, the present invention can be applied to color printers or multi-color printers. In addition, the present invention also can be applied to other fields, such as fuel injection systems, cell sorting, drug delivery systems, print lithography, micro inject propulsion systems, and others.

According to the present invention, only a single poly-silicon process and a single metal process are used to complete circuit layouts of the whole chip. There are several advantages of the present invention. The fluid injection head of the present invention uses two fewer photo masks than other similar products and therefore the cost of the photolithography processes are reduced. Moreover, fabricating time is reduced and throughput is improved. Since ink is supplied without the requirement of etching through the entire chip, the circuit layouts can be performed above the manifolds, leading to a reduction in wafer size and an increase the number of dies per wafer. Using this method of improving layout integration, the area required for circuit layout is reduced, and more orifices can be disposed in the same wafer area to improve the printing speed.

Those skilled in the art will readily observe that numerous modifications and alterations of the device may be made while retaining the teachings of the invention. Accordingly, the above disclosure should be construed as limited only by the metes and bounds of appended claims.

What is claimed is:

1. A method for fabricating a fluid injection head structure comprising steps of:
    providing a substrate;
    forming at least one bubble generator on the substrate;
    forming at least one functional device;
    forming a first conductive trace, the first conductive trace formed of poly-silicon; and
    forming a second conductive trace, which is used to electrically couple the functional device with the bubble generator, and also serves to couple the functional device with the first conductive trace.

2. The method of claim 1 wherein the method further comprises forming a contact layer positioned between the first conductive trace and the second conductive trace to electrically couple the first conductive trace with the second conductive trace.

3. The method of claim 1 wherein the second conductive trace comprises a pad.

4. The method of claim 1 wherein the method further comprises a step of forming a dielectric layer between the first conductive trace and the second conductive trace.

5. The method of claim 1 wherein the functional device is a transistor comprising a source, a drain and a gate.

6. The method of claim 5 wherein the transistor is a metal oxide semiconductor field effect transistor (MOSFET) and the gate is composed of a poly-silicon layer.

7. The method of claim 1 wherein the gate and the first conductive trace are formed in a same photo-etching process (PEP).

8. The method of claim 1 wherein the material of the second conductive trace is any one of aluminum, gold, copper, tungsten, alloys of aluminum-silicon-copper, and alloys of aluminum-copper.

9. The method of claim 1 wherein the bubble generator comprises a first bubble generating device and a second bubble generating device positioned adjacent to a corresponding orifice on a corresponding chamber, wherein when the chamber is full of fluid, the first bubble generating device generates a first bubble, and then the second bubble generating device generates a second bubble to eject the fluid from the chamber through the orifice.

10. The method of claim 9 wherein the first bubble serves as a virtual valve, restricts flow of fluid out of the chamber.

11. The method of claim 1 wherein the method further comprises the steps of:
    forming a dielectric layer on the substrate;
    etching the substrate and the dielectric layer to form a manifold and at least one chamber connected to the manifold such that fluid can flow through the manifold to the chamber; and
    forming at least one orifice positioned adjacent to the corresponding bubble generator, which is connected to the chamber for ejecting the fluid.

12. The method of claim 11 wherein the method further comprises a step of:

forming a low stress layer, wherein the bubble generator is formed on the low stress layer.

13. The method of claim 11 wherein the injection head is used as a print head of an inkjet printer, the manifold is connected to an ink cartridge, and the fluid is the ink of ink cartridge.

14. The method of claim 1 wherein at least one layer of the functional device is formed on a same poly-silicon layer as the first conductive trace.

15. The method of claim 6 wherein the gate of the MOSFET is formed on a same poly-silicon layer as the first conductive trace.

* * * * *